(12) United States Patent
Hassan et al.

(10) Patent No.: US 8,497,296 B2
(45) Date of Patent: Jul. 30, 2013

(54) N,N'-HYDRAZINO-BIS-ISATIN DERIVATIVES WITH SELECTIVE ACTIVITY AGAINST MULTIDRUG-RESISTANT CANCER CELLS

(75) Inventors: Tarek Aboul-Fadl Mohamed Hassan, Riyadh (SA); Adnan Ahmed Kadi, Riyadh (SA); Hatem Abdel-Khader Abdel-Aziz, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/423,040

(22) Filed: Mar. 16, 2012

(65) Prior Publication Data

US 2012/0252860 A1 Oct. 4, 2012

(30) Foreign Application Priority Data

Mar. 31, 2011 (EP) .................................. 11160557

(51) Int. Cl.
*A61K 31/404* (2006.01)
*C07D 403/12* (2006.01)

(52) U.S. Cl.
USPC ........................................ 514/414; 548/461

(58) Field of Classification Search
None
See application file for complete search history.

(56) References Cited

PUBLICATIONS

Abdou, W. M.; Ganoub, N. A. F. General Approach for Regioselective Synthesis of Fused Phosphono Substituted-Oxadiazines. Heteratom Chemistry. 2000, 11, 196-204.*
Chemical Abstract Registry No. 485763-70-0, indexed in the Registry File on STN CAS Online Feb. 5, 2003.*
Chemical Abstract Registry No. 503014-33-3, indexed in the Registry File on STN CAS Online Apr. 15, 2003.*
Chemical Abstract Registry No. 899624-64-7, indexed in the Registry File on STN CAS Online Auguest 8, 2006.*
W. A. Milaat, Knowledge of secondary-school female students on breast cancer and breast self-examination in Jeddah, Saudi Arabia. East. Mediterr. Health J., 6(2/3), 338-343 (2000), (English translation only).
M. Baringa. From bench top to bedside. *Science*, 278(5340), pp. 1036-1039 (Nov. 7, 1997).
A. Jemal, R. Siegel, E. Ward, Y. Hao, J. Xu, T. Murray, M. J. Thun, Cancer Statistics, 2008. *CA Cancer J Clinic*, 58, pp. 71-96 (2008).
R. Sinha, K. El-Bayoumy, Apoptosis is a critical cellular even in cancer chemoprevention and chemotherapy by selenium compounds. *Current Cancer Drug Targets*, 4(13) (2004).
P. Cozzi, N. Mongelli, A. Suarato, Recent Anticancer Cytotoxic Agents. *Curr. Med. Chem.—Anti-Cancer Agents*, 4(93). pp. 93-121. 2004.
A. Ezzat, E. M. Ibrahim, M. A. Raja, S. Al-Sobhi, A. Rostom, R. K. Stuart. Locally advanced breast cancer in Saudi Arabia: high frequency of stage III in a young population. Med. Oncol., 16, 95-103 (1999).

Talal J. Hashim. Adolescents and cancer: a survey of knowledge and attitudes about cancer in eastern province of Saudi Arabia. *Journal of Family & Community Medicine: Adolescents and Cancer*, 7(3), pp. 29-35. (2000) (Retrieved from www.jfcmonline.com on Aug. 4, 2012).
http://www.who.int/ncd_surveillance/infobase/web/InfoBasePolicyMaker/reports/ReporterFullView (Retrieved from the Internet on Sep. 4, 2012).
Amal Al-Sibai, Dealing with the growing rate of cancer in the Kingdom. *Saudi Gazette*. http://www.gulfoncology.org/blog/2007/06/cancer-incidence-on-rise-in-saudi.html (Retrieved from the Internet on Sep. 5, 2012).
J. M. Nabholtz, D. Slamon. New adjuvant strategies for breast cancer: Meeting the challenge of integrating chemotherapy and trastuzumab (Herceptin). *Semin. Oncol.* 28(1) (Suppl 3), 1-12 (2001).
I. Pastan and R. J. Kreitman. Immunotoxins for targeted cancer therapy. *Adv. Drug Deliv. Rev.*, 31, 53-88 (1998).
Druker BJ, Sawyers CL, Kantarjian H, et al. Activity of a specific inhibitor of the BCR-ABL tyrosine kinase in the blast crisis of chronic myeloid leukemia and acute lymphoblastic leukemia with the Philadelphia chromosome. *N. Engl. J. Med. 344*, 1038-42 (2001).
Akan, S. Akan, H. Akca, B. Savas, T. Oznen, N-acetylcysteine enhances multidrug resistance-associated protein mediated doxorubicin resistance. *Eur. J. Clin. Invest.* 34, 683-689 (2004).
Akan, S. Akan, H. Akca, B. Savas, T. Ozben, Multidrug resistance-associated protein 1 (MRP1) mediated vincristine resistance: effects of N-acetylcystein and Buthionine sulfoximine. Cancer Cell Int. 5, 22 (2005).
M. Liscovitch, Y. Lavie, Cancer multidrug resistance: a review of recent drug discovery research. IDrugs, 5(4), 349-355 (2002).

(Continued)

*Primary Examiner* — Jason M Nolan
*Assistant Examiner* — Po-Chih Chen
(74) *Attorney, Agent, or Firm* — Ladas & Parry, LLP

(57) ABSTRACT

The invention is directed to a compound of Formula (I),

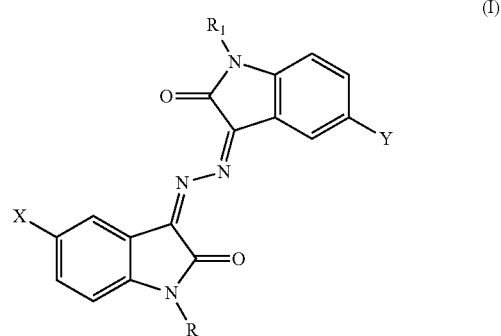

wherein R is selected from the group consisting of hydrogen atom and unsubstituted or substituted phenyl group; $R_1$ is selected from the group consisting of hydrogen atom and unsubstituted or substituted phenyl group; X is selected from the group consisting of hydrogen atom or halogen atom; and Y is selected from the group consisting of hydrogen atom, halogen atom, $C_1$-$C_4$ alkyl group, nitro group, and —$OCF_3$ group, as well as for its use in therapy, preferably for the treatment of cancer, and to a related pharmaceutical composition, the use of the compound for the manufacture of a medicament for the respective medical indication, and a method of synthesis of the compounds of the invention.

11 Claims, No Drawings

PUBLICATIONS

H. Thomas, H.M. Coley, Overcoming multidrug resistance in cancer: an update on the clinical strategy of inhibiting p-glycoprotein. *Cancer Control*, 10(2), 159-165 (2003).

C. H. Choi, ABC transporters as multi drug resistance mechanism and the development of chemosensitizers for their reversal. *Cancer Cell Int.* 5, 30 (2005).

S. V. Ambudkar, S. Dey, C. A. Hrycyna, M. Ramachandra, I. Pastan, M. M. Gottesman, Biochemical, Cellular, and pharmacological aspects of the multidrug transporter. *Annu. Rev. Pharmacol. Toxicol.* 39, 361-398 (1999) (retrieved from arjournals.annualreviews.org by Purdue University Library on Mar. 4, 2005).

R. Krishna, L.D. Mayer, Multidrug resistance (MDR) in cancer. Mechanisms, reversal using modulators of MDR and the role of MDR modulators in influencing the pharmacokinetics of anticancer drugs. *Eur. J. Pharm. Sci. 11*, 265-283 (2000).

A.A. Stavrovskaya, Cellular mechanisms of multidrug resistance of tumor cells. *Biochemistry (Mosc).* 65(1), 95-106 (2000).

S. Grimaudo, M. Tolomeo, A. chimirri, M. Zappala, R. A. Gancitano, N. D'Alessandro, Selective induction of apoptosis in multidrug resistant HL60R cells by the thiazolobenzoimidazole derivative 1-(2, 6-difluorophenyl)-1$H$, 3 $H$-thiazolo [3, 4-a] benzimidazole (TBZ). *European Journal of Cancer*, 34(11), pp. 1756-1763. (1998).

Z.H. Zhu, In Dan Xi Xin Fa; Y. Wang, J.P. Zhu, L.Z. Jiang, Eds.; People's medical publishing, 2005, ISBN 7:117-06711-X/R_6715, (English translation only).

W. Tang, G. Eisenbrand, Chinese drugs of plant origin: Chemistry, Pharmacology, and Use in Traditional and Modern Medicine. *Phytochemistry*32(4). p. 1081, 1993.

H.A. Abdel-Aziz, A.Bari, T. Aboul-Fadi and S. Weng Ng. (Z)-3-Hydrazinylidene-1-phenylindolin-2-one. *Organic Compounds: Acta Crystallographica Section E* (2010).

J.A. Ludwig, G. Szakacs, S.e. Marin, B.F. Chu, C. Cardarelli, Z.E. Sauna, N.J. Caplen, H.M. Fales, S.V. Ambudkar, J.N. Weinstein, J.N.; Gottesman. Selective Toxicity of NSC73306 in MDR1-Positive Cells as a New Strategy to Circumvent Multidrug Resistance in Cancer. *Cancer Res.*, 66, 4808-4815. (Downloaded from cancerres. aacrjournals.org on Jun. 23, 2012) (2006).

\* cited by examiner

N,N'-HYDRAZINO-BIS-ISATIN DERIVATIVES WITH SELECTIVE ACTIVITY AGAINST MULTIDRUG-RESISTANT CANCER CELLS

CROSS-REFERENCE TO RELATED APPLICATIONS

This application claims priority to European Patent Application No. 11160557.2 filed on Mar. 31, 2011, the disclosure of which is incorporated herein by reference in its entirety.

BACKGROUND

Cancer is one of the most dreaded diseases of mankind, it is a leading cause of death throughout the world, currently, one in 4 deaths in the United States is due to cancer [1]. More than ten million new cancer cases occur annually, roughly half of which is in the developed countries, and the disease causes over six million deaths a year [2,3]. Recent studies revealed that cancer has become an ever-increasing problem in Saudi Arabia [4-6]. In 2005, cancer killed approximately 12,000 of Saudi people, 8000 of those people were under age of 70 [7]. Furthermore, cancer is growing in Saudi Arabia with 7,000 new cases being reported each year and the figure will reach 30,000 in 15 years, according to one expert [8]. The treatment of disseminated cancer has become increasingly aimed at molecular targets derived from studies of the oncogenes and tumor suppressors known to be involved in the development of human cancers [9]. This increase in specificity of cancer treatment, from the use of general cytotoxic agents such as nitrogen mustard in the 1940s, to the development of natural-product anticancer drugs in the 1960s such as Vinca alkaloids and anthracyclines, which are more cytotoxic to cancer cells than normal cells, to the use of specific monoclonal antibodies [10] and immunotoxins [11] targeted to cell surface receptors and specific agents that inactivate kinases in growth-promoting pathways [12], has improved the response rate in cancer and reduced side effects of anticancer treatment but has not yet resulted in cure of the majority of patients with metastatic disease. A study of the mechanisms by which cancers elude treatment has yielded a wealth of information about why these therapies fail and is beginning to yield valuable information about how to circumvent drug resistance in cancer cells and/or design agents that are not subject to the usual means of resistance.

The failure of the curative treatment of cancer patients often occurs as a result of intrinsic or acquired drug resistance of the tumor to chemotherapeutic agents. The resistance of tumors occurs not only to a single cytotoxic drug used, but also occurs as a cross-resistance to a whole range of drugs with different structures and cellular targets. This phenomenon is called multiple drug resistance (MDR). Once MDR appears, using high doses of drugs to overcome resistance is ineffective, toxic effects appear and resistance are further stimulated. Multidrug resistance (MDR) severely limits the effectiveness of chemotherapy in a variety of common malignancies and is responsible for the overall poor efficacy of cancer chemotherapy [13-17].

The cytotoxic drugs that are most frequently associated with MDR are hydrophobic, amphipathic natural products, such as the taxanes (paclitaxel and docetaxel), vinca alkaloids (vinorelbine, vincristine, and vinblastine), anthracyclines (doxorubicin, daunorubicin, and epirubicin), epipodophyllotoxins (etoposide and teniposide), antimetabolites (methorexate, fluorouracil, cytosar, 5-azacytosine, 6-mercaptopurine, and gemcitabine), topotecan, dactinomycin, and mitomycin C [16,18-20].

In spite of the large number of available chemotherapeutic agents the medical need is still largely unmet. The main reasons are: the lack of selectivity of conventional drugs, leading to toxicity; the metastatic spreading, implying early tumor implantation in organs other than primary site; the heterogeneity of the disease, comprising about 100 types of cancer; the intrinsic or acquired resistance to chemotherapy developed after few therapeutic cycles, i.e. multi-drug resistance (MDR) [21]. Therefore, new drugs that offer improvements over current therapies are desperately needed. New chemical entities with novel mechanisms of action will most likely possess activity against MDR cancer. [MDR severely limits the effectiveness of chemotherapy in a variety of common malignancies and is responsible for the overall poor efficacy of cancer chemotherapy [19-23].]

SUMMARY OF THE INVENTION

Accordingly, the present invention describes design, synthesis and antiproliferative activity of novel N,N''-hydrazino-bis(isatin) derivatives with the following general structure (I)

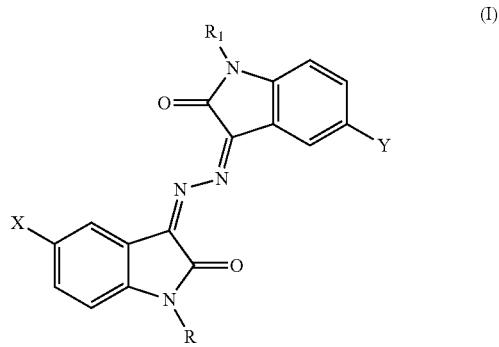

wherein
R is selected from the group consisting of hydrogen atom and unsubstituted or substituted phenyl group;
$R_1$ is selected from the group consisting of hydrogen atom and unsubstituted or substituted phenyl group;
X is selected from the group consisting of hydrogen atom or halogen atom; and
Y is selected from the group consisting of hydrogen atom, halogen atom, $C_1$-$C_4$ alkyl group, nitro group, and —$OCF_3$ group.

In one embodiment of the present invention, R is selected from the group consisting of hydrogen atom and unsubstituted phenyl group.

In another embodiment of the invention, $R_1$ is selected from the group consisting of hydrogen atom and unsubstituted phenyl group.

In a further embodiment of the invention, X is selected from the group consisting of hydrogen atom and fluorine atom.

In still further embodiment of the invention, Y is selected from the group consisting of hydrogen atom, fluorine atom, chlorine atom, bromine atom, methyl group, nitro group and —$OCF_3$ group.

Moreover, the present invention is also related to a compound according to the present invention for use in therapy, preferably for the treatment of cancer and most preferably for the treatment of multidrug resistant cancer.

Further, the present invention is directed to a pharmaceutical composition comprising a compound according to the present invention together with at least one pharmaceutically acceptable excipient.

In a further embodiment, the present invention is directed to the use of a compound according to the present invention for the manufacture of a medicament for the treatment of cancer, most preferably for the treatment of multidrug resistant cancer.

The present invention is also related to a method of synthesis of a compound according to claim 1, wherein
(i) an isatin of Formula (1) is reacted with hydrazine or a hydrazine hydrate to obtain a hydrazone of Formula (2),

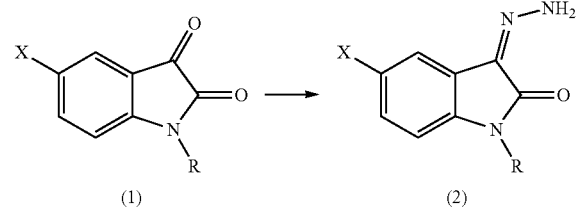

wherein R and X are as defined in claim 1; and
(ii) reacting the hydrazone obtained in step (i) with an isatin of formula (1')

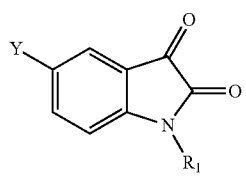

to obtain a compound of formula (1), wherein $R_1$ and Y are as defined hereinabove.

Preferably, step (i) and (ii) are conducted in a polar organic solvent, preferably methanol in step (i) and ethanol/acid in step (ii).

In a preferred embodiment, step (i) and (ii) are independently conducted either under reflux conditions or with a microwave assisted method.

DETAILED DESCRIPTION OF THE INVENTION

1. General Synthesis of the Target Compounds

The general procedures for the preparation of the target derivatives of isatin is described in Schemes 1 and 2.

Scheme 1.

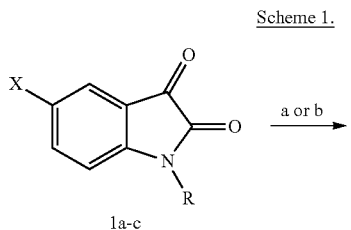

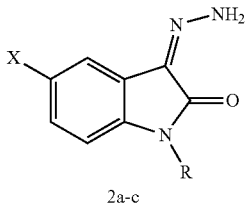

1a, R = H; X = H
1b, R = Ph; X = H
1c, R = H; X = F

Reagents and conditions: (a) NH$_2$NH$_2$·H$_2$O, MeOH, MWI, 50 W (90° C.), 1 min, 85-90%; (b) NH$_2$NH$_2$·H$_2$O, MeOH, reflux 1 h, 69-77%.

Scheme 2.

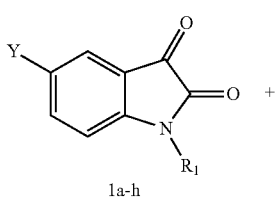

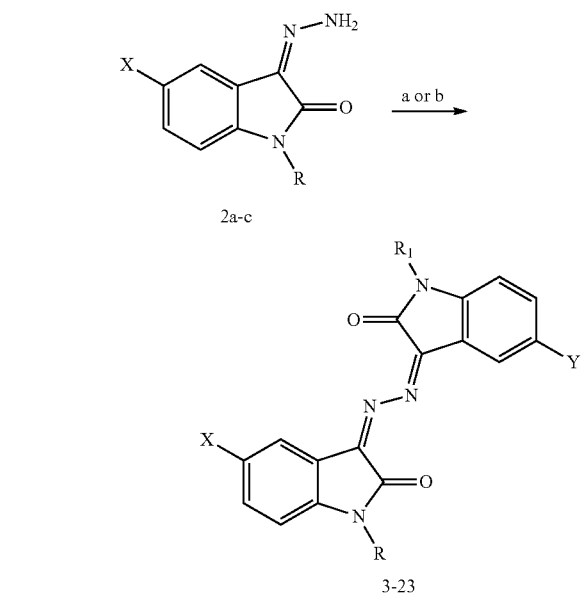

(a) EtOH/AcOH, MWI, 50 W (90° C.), 7 min, 72-95%; (b) EtOH/AcOH, reflux 4-6 h, 66-89%.

The target compounds can be synthesized via the reaction of the appropriate isatin with hydrazine hydrate to get the corresponding (Z)-3-hydrazinyl-indene-1-H— or 1-phenyl-indolin-2-one (2a-c) [24], Scheme 1. 2a-c can be achieved by conventional method or microwave, assisted method (MWI). Target compounds can also be obtained by conventional method or MWI through coupling the appropriate isatin derivatives with 2a-c as illustrated by scheme 2.

The synthesized compounds were purified by flash chromatography and crystallized from ethanol. The structures were confirmed by spectroscopic methods of analyses. Structures of these targets are given in Table 1.

TABLE 1

Structure of reactants isatins 1a-h, hydrazones 2a-c and products 3-23

| Isatin 1a-h | Hydrazone 2a-c | Products 3-23 |
|---|---|---|
| 1a | 2a | 3 |
| 1b | 2a | 4 |
| 1c | 2a | 5 |
| 1d | 2a | 6 |

TABLE 1-continued

Structure of reactants isatins 1a-h, hydrazones 2a-c and products 3-23

| Isatin 1a-h | Hydrazone 2a-c | Products 3-23 |
|---|---|---|
| 1e | 2a | 7 |
| 1f | 2a | 8 |
| 1g | 2a | 9 |
| 1h | 2a | 10 |

TABLE 1-continued

Structure of reactants isatins 1a-h, hydrazones 2a-c and products 3-23

| Isatin 1a-h | Hydrazone 2a-c | Products 3-23 |
|---|---|---|
| 1b | 2b | 11 |
| 1c | 2b | 12 |
| 1d | 2b | 13 |
| 1e | 2b | 14 |

TABLE 1-continued
Structure of reactants isatins 1a-h, hydrazones 2a-c and products 3-23
| Isatin 1a-h | Hydrazone 2a-c | Products 3-23 |
|---|---|---|
| 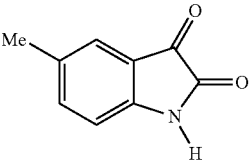 [SMILES: Cc1ccc2c(c1)C(=O)C(=O)N2] 1f | 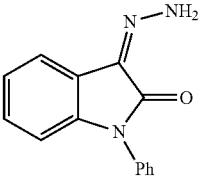 [SMILES: N/N=C1\C(=O)N(c2ccccc2)c2ccccc21] 2b | 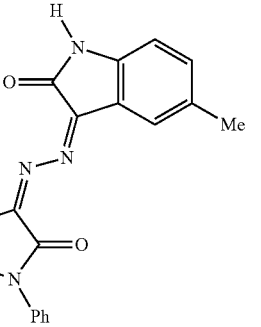 15 |
| 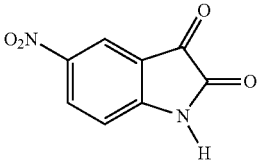 [SMILES: O=C1Nc2ccc([N+](=O)[O-])cc2C1=O] 1g | 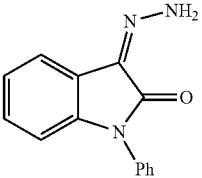 [SMILES: N/N=C1\C(=O)N(c2ccccc2)c2ccccc21] 2b | 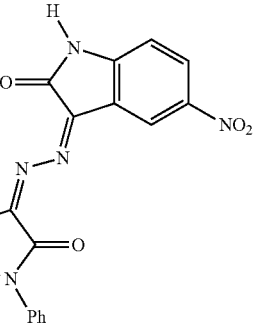 16 |
| 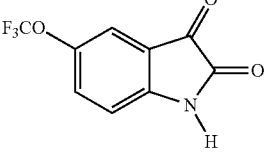 1h | 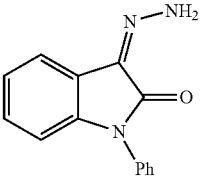 [SMILES: N/N=C1\C(=O)N(c2ccccc2)c2ccccc21] 2b | 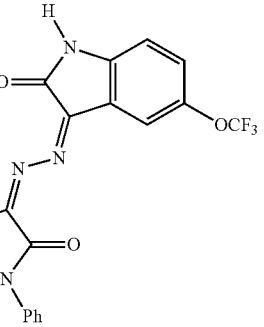 17 |
| 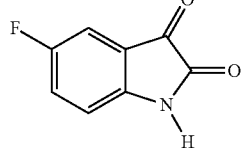 1c | 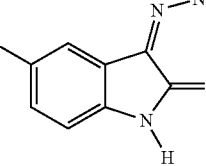 2c | 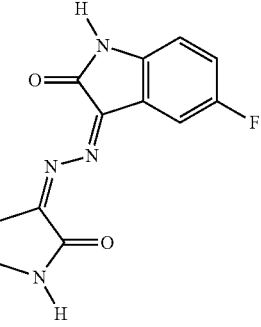 18 |

TABLE 1-continued
Structure of reactants isatins 1a-h, hydrazones 2a-c and products 3-23
| Isatin 1a-h | Hydrazone 2a-c | Products 3-23 |
|---|---|---|
| 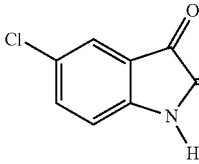<br>1d | 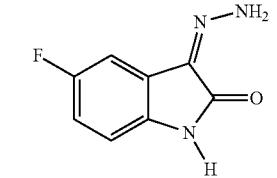 [SMILES: N/N=C1\C(=O)Nc2ccc(F)cc21]<br>2c | 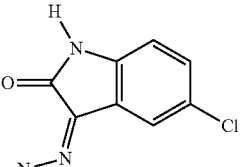<br>19 |
| 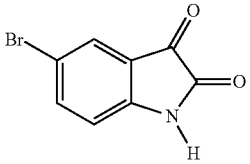 [SMILES: O=C1Nc2ccc(Cl)cc2C1=O]<br>1e | 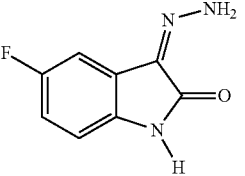 [SMILES: N/N=C1\C(=O)Nc2ccc(F)cc21]<br>2c | 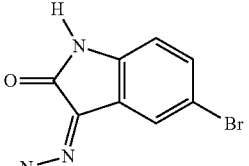<br>20 |
| 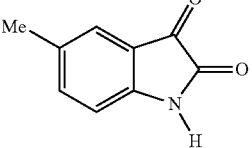<br>1f | 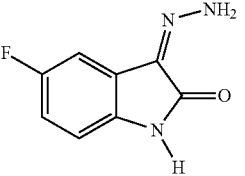 [SMILES: N/N=C1\C(=O)Nc2ccc(F)cc21]<br>2c | 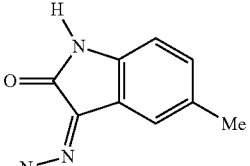<br>21 |
| 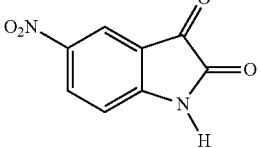<br>1g | 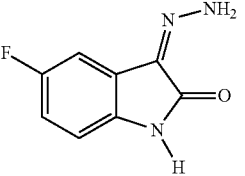 [SMILES: N/N=C1\C(=O)Nc2ccc(F)cc21]<br>2c | 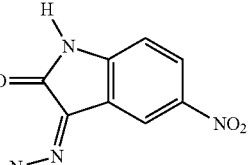<br>22 |

TABLE 1-continued

Structure of reactants isatins 1a-h, hydrazones 2a-c and products 3-23

| Isatin 1a-h | Hydrazone 2a-c | Products 3-23 |
|---|---|---|
| 1h | 2c | 23 |

2. Synthesis of hydrazones 2a-c 2.1. Conventional Method: A mixture of isatins 1a-c (1 mmol) and hydrazine hydrate (99%, 0.055 g, 1.1 mmol) in absolute methanol (25 ml) was refluxed for 1 h, and then cooled to room temperature. The precipitate of hydrazones was filtered and dried. The crude product was recrystallized from EtOH/DMF to give hydrazones 2a-c in 69-77% yield.

2.2. Microwave Method: The appropriate isatins 1a-c (1 mmol) and hydrazine hydrate (99%, 0.055 g, 1.1 mmol) in absolute methanol (10 ml) were placed in the tube of microwave reactor and irradiated at 90° C. for 1 min. The temperature of the reaction mixture was adjusted by the computer of the microwave device. Then left to cool, the resulting residue was recrystallised from EtOH/DMF to afford the corresponding hydrazones 2a-c in 85-90% yield.

3. Synthesis of bis-indolin-2-ones 3-23

3.1. Conventional Method: A mixture of hydrazones 2a-c (1 mmol) and isatins 1a-h (1 mmol) in ethanol (25 ml) was refluxed for 4-6 h, and then cooled to room temperature. The precipitate was filtered and dried. The crude product was recrystallized from EtOH/DMF to obtain compounds 3-23 in 66-89% yield.

3.2. Microwave Method: A solution of hydrazones 2a-c (1 mmole) and isatins 1a-h (1 mmole) in ethanol (15 ml) were prepared. Few drops of glacial acetic acid were added and whole reaction mixture was irradiated under microwave irradiation at 90° C. for 7 minutes. The reaction mixture was cooled. The solid that separated on cooling was filtered, washed with cold ethanol, dried and recrystallised from EtOH/DMF.

4. Spectroscopical Data of the Synthesized Compounds

(Z)-3-Hydrazonoindolin-2-one (2a)

IR (KBr) v 3361-3199 (NH, NH$_2$), 1687 (C=O), 1609 (C=N) cm$^{-1}$; $^1$H NMR (DMSO-d$_6$) δ 6.87 (d, 1H, J=7.0 Hz, ArH), 6.97 (t, 1H, J=6.5 Hz, ArH), 7.16 (t, 1H, J=6.5 Hz, ArH), 7.37 (d, 1H, J=7.0 Hz, ArH), 9.57 (d, 1H, J=14.0 Hz, D$_2$O exch., amino H), 10.56 (d, 1H, J=14.0 Hz, D$_2$O exch., -amino H), 10.71 (s, D$_2$O exch., 1H, NH); $^{13}$C NMR δ 109.93, 117.43, 121.32, 126.17, 127.0, 162.75; MS m/z (%) 161 (M$^+$, 39.7), 103.7 (64.3), 46.8 (100).

(Z)-5-Fluoro-3-hydrazonoindolin-2-one (2b)

IR (KBr) v 3365-3153 (NH, NH$_2$), 1682 (C=O), 1585 (C=N) cm$^{-1}$; $^1$H NMR (DMSO-d$_6$) δ 6.85 (m, 1H, ArH), 6.97 (m, 1H, ArH), 7.15 (d, 1H, J=7.5 Hz, ArH), 9.81 (d, 1H, J=15.0 Hz, D$_2$O exch., amino H), 10.65 (d, 1H, J=15.0 Hz, D$_2$O exch., amino H), 10.72 (s, D$_2$O exch., 1H, NH); $^{13}$C NMR δ 104.30 ($^2$J$_{F-C}$=25.3 Hz), 110.74 ($^3$J$_{F-C}$=8.3 Hz), 113.10 ($^2$J$_{F-C}$=24.2 Hz), 123.59 ($^3$J$_{F-C}$=9.2 Hz), 125.65, 134.69, 158.10 ($^1$J$_{F-C}$=235.3 Hz), 162.95; MS m/z (%) 179 (M$^+$, 11.8), 61.9 (55.7), 40.1 (100).

(Z)-3-Hydrazono-1-phenylindolin-2-one (2c)

IR (KBr) v 3375-3208 (NH$_2$), 1674 (C=O), 1592 (C=N) cm$^{-1}$; $^1$H NMR (DMSO-d$_6$) δ 6.82 (m, 1H, ArH), 7.11 (m, 1H, ArH), 7.20 (m, 1H, ArH), 7.43-7.53 (m, 4H, ArH), 7.59 (m, 2H, ArH), 9.90 (d, 1H, J=15.0 Hz, D$_2$O exch., amino H), 10.61 (d, 1H, J=14.5 Hz, D$_2$O exch., amino H); $^{13}$C NMR δ 109.06, 117.51, 122.52, 124.63, 126.63, 126.98, 127.86, 129.44, 129.51, 133.79, 139.44, 159.98; MS m/z (%) 237.1 (M$^+$, 100), 192 (60.1), 51 (93.6).

(3Z,3'Z)-3,3'-(Hydrazine-1,2-diylidene)diindolin-2-one (3)

IR (KBr) v 3276 (2NH), 1722 (2C=O), 1615 (2C=N) cm$^{-1}$; $^1$H NMR (DMSO-d$_6$) δ 6.92 (d, 2H, J=7.5 Hz, ArH), 7.02 (t, 1H, J=7.5 Hz, ArH), 7.43 (t, 1H, J=7.5 Hz, ArH), 7.51 (d, 1H, J=7.5 Hz, ArH), 11.02 (s, 2H, 2NH); $^{13}$C NMR δ 111.09, 115.75, 122.53, 128.17, 134.39, 144.70, 145.16, 163.39; MS m/z (%) 290.5 (M$^+$, 6.6), 46 (74.9), 40.1 (100).

(Z)-3-((Z)-(2-Oxoindolin-3-ylidene)hydrazono)-1-phenylindolin-2-one (4)

IR (KBr) v 3448 (NH), 1734 (2C=O), 1606 (2C=N) cm$^{-1}$; MS m/z (%) 266.1 (M$^+$, 3.5), 40.1 (100).

(Z)-5-Fluoro-3-((Z)-(2-oxoindolin-3-ylidene)hydrazono)indolin-2-one (5)

IR (KBr) v 3420-3284 (2NH), 1722 (2C=O), 1616 (2C=N) cm$^{-1}$; $^1$H NMR (DMSO-d$_6$) δ 6.92-7.53 (m, 7H,

ArH), 11.02 (s, D₂O exch., 2H, 2NH); ¹³C NMR δ 111.09, 112.12 ($^3J_{F-C}$=7.4 Hz), 115.0 ($^2J_{F-C}$=25.7 Hz), 115.77, 116.20 ($^3J_{F-C}$=8.6 Hz), 120.77 ($^2J_{F-C}$=23.7 Hz), 122.52, 128.48, 134.59, 141.56, 144.70, 145.16, 145.44, 145.64, 157.50 ($^1J_{F-C}$=263.0 Hz), 163.39, 163.44; MS m/z (%) 308.2 (M⁺, 5.0), 46 (100).

(Z)-5-Chloro-3-((Z)-(2-oxoindolin-3-ylidene)hydrazono)indolin-2-one (6)

IR (KBr) v 3420-3244 (2NH), 1736 (2C=O), 1617 (2C=N) cm⁻¹; ¹H NMR (DMSO-d₆) δ 6.86-7.58 (m, 7H, ArH), 11.03 (s, D₂O exch., 2H, 2NH); MS m/z (%) 325.2 (M'+1, 6.8), 324.4 (M⁺, 15), 78 (100).

(Z)-5-Bromo-3-((Z)-(2-oxoindolin-3-ylidene)hydrazono)indolin-2-one (7)

IR (KBr) v 3239 (2NH), 1735 (2C=O), 1612 (2C=N) cm⁻¹; ¹H NMR (DMSO-d₆) δ 6.88-7.66 (m, 7H, ArH), 11.02 (s, D₂O exch., 1H, NH), 11.15 (s, D₂O exch., 1H, NH); ¹³C NMR δ 111.11, 113.05, 113.64, 115.79, 117.48, 122.52, 125.05, 128.62, 130.34, 134.62, 136.52, 144.35, 144.76, 145.43, 145.91, 163.06, 163.43; MS m/z (%) 369 (M⁺, 19.0), 40.1 (100).

(Z)-5-Methyl-3-((Z)-(2-oxoindolin-3-ylidene)hydrazono)indolin-2-one (8)

IR (KBr) v 3286 (2NH), 1723 (2C=O), 1615 (2C=N) cm⁻¹; ¹H NMR (DMSO-d₆) δ 2.21 (s, 3H, CH₃), 6.82-7.53 (m, 7H, ArH), 11.01 (s, D₂O exch., 2H, 2NH); ¹³C NMR δ 20.53, 110.87, 111.08, 115.75, 122.53, 128.17, 128.48, 131.42, 134.39, 134.74, 142.94, 144.70, 144.81, 145.16; MS m/z (%) 303.9 (M⁺, 4.0), 40.1 (100).

(Z)-5-Nitro-3-((Z)-(2-oxoindolin-3-ylidene)hydrazono)indolin-2-one (9)

IR (KBr) v 3447 (2NH), 1731 (2C=O), 1617 (2C=N) cm⁻¹; ¹H NMR (DMSO-d₆) δ 6.93-8.36 (m, 7H, ArH), 11.06 (s, D₂O exch., 1H, NH), 11.69 (s, D₂O exch., 1H, NH); MS m/z (%) 335 (M⁺, 9.7), 47.8 (100).

(Z)-3-((Z)-(2-Oxoindolin-3-ylidene)hydrazono)-5-(trifluoromethoxy)indolin-2-one (10)

IR (KBr) v 3446-3245 (2NH), 1740 (2C=O), 1617 (2C=N) cm⁻¹; ¹H NMR (DMSO-d₆) δ 6.92-7.56 (m, 7H, ArH), 11.02 (s, D₂O exch., 1H, NH), 11.20 (s, D₂O exch., 1H, NH); ¹³C NMR δ 111.11, 112.18, 115.72, 116.42, 121.12, 122.54, 127.20, 128.67, 134.69, 142.95, 144.26, 145.15, 145.49, 146.00, 159.38, 163.36, 163.43; MS m/z (%) 374 (M⁺, 7.9), 44.9 (100).

(3Z,3'Z)-3,3'-(Hydrazine-1,2-diylidene)bis(1-phenylindolin-2-one) (11)

IR (KBr) v 1731 (2C=O), 1605 (2C=N) cm⁻¹; ¹H NMR (DMSO-d₆) δ 6.82-7.78 (m, 18H, ArH); ¹³C NMR δ 110.03, 115.47, 123.53, 126.92, 128.48, 128.62, 129.67, 133.48, 134.38, 144.11, 146.18, 161.53; MS m/z (%) 442.2 (M⁺, 3.3), 64 (100).

(Z)-5-Fluoro-3-((Z)-(2-oxo-1-phenylindolin-3-ylidene)hydrazono)indolin-2-one (12)

IR (KBr) v 3282 (NH), 1735 (2C=O), 1608 (2C=N) cm⁻¹; ¹H NMR (DMSO-d₆) δ 6.82-7.67 (m, 12H, ArH), 11.07 (s, D₂O exch., 1H, NH); MS m/z (%) 384.2 (M⁺, 3.5), 48 (100).

(Z)-5-Chloro-3-((Z)-(2-oxo-1-phenylindolin-3-ylidene)hydrazono)indolin-2-one (13)

IR (KBr) v 3448 (NH), 1736 (2C=O), 1609 (2C=N) cm⁻¹; ¹H NMR (DMSO-d₆) δ 6.83-7.63 (m, 12H, ArH), 11.18 (s, D₂O exch., 1H, NH); MS m/z (%) 400.1 (M⁺, 5.1), 63 (100).

(Z)-5-Bromo-3-((Z)-(2-oxo-1-phenylindolin-3-ylidene)hydrazono)indolin-2-one (14)

IR (KBr) v 3448 (NH), 1734 (2C=O), 1608 (2C=N) cm⁻¹; MS m/z (%) 444.7 (M⁺, 1.8), 43.8 (100).

(Z)-5-Methyl-3-((Z)-(2-oxo-1-phenylindolin-3-ylidene)hydrazono)indolin-2-one (15)

IR (KBr) v 3447 (NH), 1736 (2C=O), 1609 (2C=N) cm⁻¹; ¹H NMR (DMSO-d₆) δ 2.20 (s, 3H, CH₃), 6.83-7.63 (m, 12H, ArH), 11.18 (s, D₂O exch., 1H, NH); MS m/z (%) 379.9 (M⁺, 7.4), 62.9 (100).

(Z)-5-Nitro-3-((Z)-(2-oxo-1-phenylindolin-3-ylidene)hydrazono)indolin-2-one (16)

IR (KBr) v 3447 (NH), 1740 (2C=O), 1609 (2C=N) cm⁻¹; MS m/z (%) 411.1 (M⁺, 1.7), 45.8 (100).

((Z)-3-(Z)-(2-oxo-1-phenylindolin-3-ylidene)hydrazono)-5-(trifluoromethoxy)indolin-2-one (17)

IR (KBr) v 3236 (NH), 1747 (2C=O), 1608 (2C=N) cm⁻¹; MS m/z (%) 449.6 (M⁺, 2.7), 49.9 (100).

(3Z,3'Z)-3,3'-(Hydrazine-1,2-diylidene)bis(5-fluoroindolin-2-one) (18)

IR (KBr) v 3252 (2NH), 1739 (2C=O), 1625 (2C=N) cm⁻¹; ¹H NMR (DMSO-d₆) δ 6.93-7.33 (m, 6H, ArH), 11.04 (s, D₂O exch., 2H, 2NH); ¹³C NMR δ112.12 ($^3J_{F-C}$=7.2 Hz), 115.20 ($^2J_{F-C}$=25.5 Hz), 116.24 ($^3J_{F-C}$=9.2 Hz), 120.90 ($^2J_{F-C}$=23.8 Hz), 141.82, 145.93, 157.50 ($^1J_{F-C}$=238.0 Hz), 163.49; MS m/z (%) 326 (M⁺, 11), 44.9 (100).

(Z)-5-Chloro-3-((Z)-(5-fluoro-2-oxoindolin-3-ylidene)hydrazono)indolin-2-one (19)

IR (KBr) v 3245 (2NH), 1736 (2C=O), 1618 (2C=N) cm⁻¹; ¹H NMR (DMSO-d₆) δ 6.94-7.54 (m, 6H, ArH), 11.04 (s, D₂O exch., 1H, NH), 11.14 (s, D₂O exch., 1H, NH); ¹³C NMR δ 112.08 ($^3J_{F-C}$=7.5 Hz), 112.60, 115.35 ($^2J_{F-C}$=25.7 Hz), 116.26 ($^3J_{F-C}$=8.9 Hz), 117.05, 120.90 ($^2J_{F-C}$=23.9 Hz), 126.03, 127.82, 133.89, 141.81, 144.24, 145.59, 146.13, 157.50 ($^1J_{F-C}$=237.9 Hz), 163.24, 163.50; MS m/z (%) 342 (M⁺, 17.9), 63 (100).

(Z)-5-Bromo-3-((Z)-(5-fluoro-2-oxoindolin-3-ylidene)hydrazono)indolin-2-one (20)

IR (KBr) v 3245 (2NH), 1735 (2C=O), 1616 (2C=N) cm⁻¹; ¹H NMR (DMSO-d₆) δ 6.89-7.66 (m, 6H, ArH), 11.04

(s, D$_2$O exch., 1H, NH), 11.14 (s, D$_2$O exch., 1H, NH); $^{13}$C NMR δ 112.14 ($^3J_{F-C}$=7.0 Hz), 113.06, 113.61, 115.37 ($^2J_{F-C}$=25.3 Hz), 116.24 ($^3J_{F-C}$=8.9 Hz), 117.54, 120.90 ($^2J_{F-C}$=23.7 Hz), 130.57, 136.69, 141.81, 144.61, 145.50, 146.18, 157.50 ($^1J_{F-C}$=238.0 Hz), 163.11, 163.50; MS m/z (%) 387 (M$^+$, 8.5), 46.9 (100).

(Z)-5-Fluoro-3-((Z)-(5-methyl-2-oxoindolin-3-ylidene)hydrazono)indolin-2-one (21)

IR (KBr) v 3392-3186 (2NH), 1735 (2C=O), 1623 (2C=N) cm$^{-1}$; $^1$H NMR (DMSO-d$_6$) δ 2.22 (s, 3H, CH$_3$), 6.81-7.33 (m, 6H, ArH), 10.91 (s, D$_2$O exch., 1H, NH), 11.02 (s, D$_2$O exch., 1H, NH); MS m/z (%) 322.3 (M$^+$, 6.9), 40.1 (100).

(Z)-5-Fluoro-3-((Z)-(5-nitro-2-oxoindolin-3-ylidene)hydrazono)indolin-2-one (22)

IR (KBr) v 3248 (2NH), 1737 (2C=O), 1624 (2C=N) cm$^{-1}$; $^1$H NMR (DMSO-d$_6$) δ 6.93-8.35 (m, 6H, ArH), 11.08 (s, D$_2$O exch., 1H, NH), 11.71 (s, D$_2$O exch., 1H, NH); MS m/z (%) 353.5 (M$^+$, 12.4), 63 (100).

(Z)-5-Fluoro-3-((Z)-(2-oxo-5-(trifluoromethoxy)indolin-3-ylidene)hydrazono)indolin-2-one (23)

IR (KBr) v 3246 (2NH), 1735 (2C=O), 1624 (2C=N) cm$^{-1}$; MS m/z (%) 392.4 (M$^+$, 8.9), 62.9 (100).

5. In Vitro Cell Lines and MTT Cytotoxicity Assay

The cytotoxicity of the prepared compounds was evaluated at Laboratory of Cell Biology, National Cancer Institute, National Institutes of Health, Bethesda, Md. 20892, Group in Biomolecular, USA, using the following protocol:

KB-3-1 cells (a HeLa deriviative) and its MDR derivative (KB-V1) were grown as previously described [24]. Cell survival was measured by the MTT (3-(4,5-dimethylthiazol-2-yl)-2,5-diphenyltetrazolium bromide) assay as previously described [24]. Briefly, cells were seeded in 100 µL of growth medium at a density of 5000 cells/well in 96-well plates and allowed to establish for 24 h, at which time serially diluted drugs were added in an additional 100 µL of growth medium. Cells were then incubated for 72 h at 37° C. in humidified 5% CO$_2$, at which time the growth medium was drawn and replaced with MTT in IMDM growth medium and incubated for 4 h. The MTT solution was then drawn from the wells, and 100 µL of acidified ethanol solution was added to each well and after 15 min absorption at 560 nm was measured. IC$_{50}$ cytotoxicity values were determined as the drug concentration that reduced the absorbance to 50% of that in untreated control wells and derived from at least three separate experiments·hours, treated with the specified compound or vehicle (0.1% DMSO final) control, and incubated at 37° C. an additional 72 hours. The effect of treatment on cell viability was determined using the luminescent Cell Titer Glo Assay (Promega). Results are given in Table 2.

Results

Variable and promising activity and selectivity revealed by the synthesized compounds against MDR cells, results are given in Table 2. Accordingly the synthesized bis-isatin derivatives are potential candidates for treatment MDR cancer.

TABLE 2

Structure of compounds considered in this study, along with IC$_{50}$ values determined against the parental KB-3-1 cell line, and the P-glycoprotein-expressing cell line KB-V1[a]

| Compound | Structure | IC$_{50}$ KB3-1 (mM) | IC$_{50}$ KBV1 (mM) | RR |
|---|---|---|---|---|
| 2a | 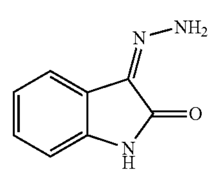 [SMILES: N/N=C1\C(=O)Nc2ccccc21] | >500 | 125.18 ± 39.39 | N/A |
| 2b | 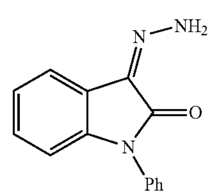 [SMILES: N/N=C1\C(=O)N(c2ccccc2)c2ccccc21] | 348.99 ± 51.65 | 198.68 ± 54.02 | 1.76 |
| 2c | 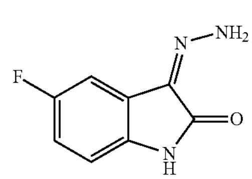 [SMILES: N/N=C1\C(=O)Nc2ccc(F)cc21] | 150.42 ± 67.67 | 31.35 ± 13.38 | 4.80 |

TABLE 2-continued

Structure of compounds considered in this study, along with $IC_{50}$ values determined against the parental KB-3-1 cell line, and the P-glycoprotein-expressing cell line KB-V1[a]

| Compound | Structure | $IC_{50}$ KB3-1 (mM) | $IC_{50}$ KBV1 (mM) | RR |
|---|---|---|---|---|
| 3 | 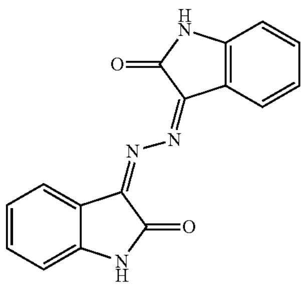 [SMILES: O=C1Nc2ccccc2/C1=N/N=C1\C(=O)Nc2ccccc21] | 17.12 ± 0.83 | 17.26 ± 1.59 | 0.99 |
| 4 | 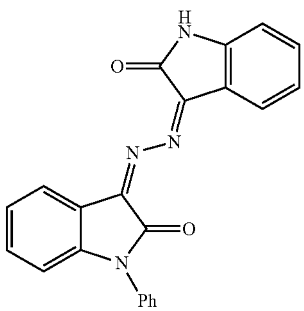 [SMILES: O=C1Nc2ccccc2/C1=N/N=C1\C(=O)N(c2ccccc2)c2ccccc21] | 8.70 ± 2.21 | 10.80 ± 1.10 | 0.81 |
| 5 | 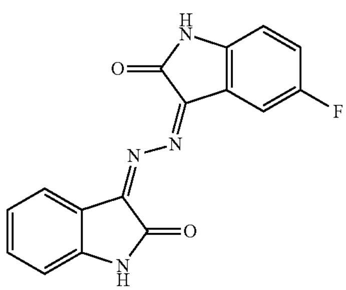 [SMILES: O=C1Nc2ccccc2/C1=N/N=C1\C(=O)Nc2ccc(F)cc21] | 28.12 ± 2.48 | 25.29 ± 10.10 | 1.11 |
| 6 | 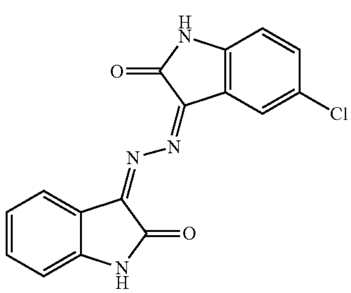 | 9.67 ± 1.74 | 7.72 ± 0.50 | 1.25 |
| 7 | 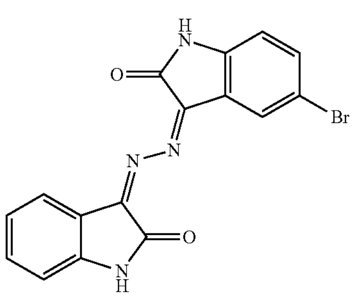 [SMILES: O=C1Nc2ccccc2/C1=N/N=C1\C(=O)Nc2ccc(Br)cc21] | 9.71 ± 0.31 | 7.58 ± 1.43 | 1.28 |

TABLE 2-continued

Structure of compounds considered in this study, along with IC$_{50}$ values determined against the parental KB-3-1 cell line, and the P-glycoprotein-expressing cell line KB-V1[a]

| Compound | Structure | IC$_{50}$ KB3-1 (mM) | IC$_{50}$ KBV1 (mM) | RR |
|---|---|---|---|---|
| 8 | (5-Me isatin bis-hydrazone) | 12.12 ± 3.14 | 14.93 ± 1.26 | 0.81 |
| 9 | (5-NO$_2$ isatin bis-hydrazone) | 29.22 ± 2.81 | 30.39 ± 6.75 | 0.96 |
| 10 | (5-OCF$_3$ isatin bis-hydrazone) | 9.75 ± 0.11 | 5.67 ± 1.18 | 1.72 |
| 11 | (N,N'-diphenyl isatin bis-hydrazone) | 25.56 ± 2.39 | 22.02 ± 2.37 | 1.16 |
| 12 | (N-Ph, 5'-F isatin bis-hydrazone) | 10.20 ± 1.52 | 11.24 ± 0.61 | 0.91 |

TABLE 2-continued
Structure of compounds considered in this study, along with IC$_{50}$ values determined against the parental KB-3-1 cell line, and the P-glycoprotein-expressing cell line KB-V1[a]
| Compound | Structure | IC$_{50}$ KB3-1 (mM) | IC$_{50}$ KBV1 (mM) | RR |
|---|---|---|---|---|
| 13 | 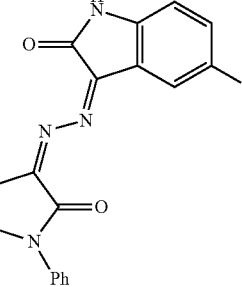 | 6.79 ± 0.63 | 6.07 ± 1.19 | 1.12 |
| 14 | 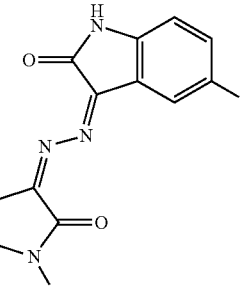 | 7.93 ± 2.11 | 8.71 ± 0.27 | 0.91 |
| 15 | 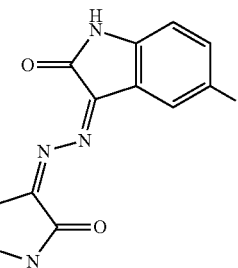 | 8.37 ± 0.62 | 8.06 ± 1.68 | 1.04 |
| 16 | 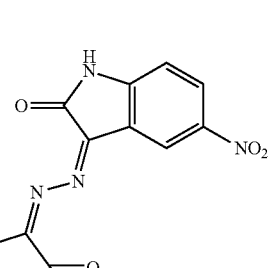 | 37.12 ± 4.05 | 48.61 ± 2.32 | 0.76 |

TABLE 2-continued

Structure of compounds considered in this study, along with IC$_{50}$ values determined against the parental KB-3-1 cell line, and the P-glycoprotein-expressing cell line KB-V1[a]

| Compound | Structure | IC$_{50}$ KB3-1 (mM) | IC$_{50}$ KBV1 (mM) | RR |
|---|---|---|---|---|
| 17 | 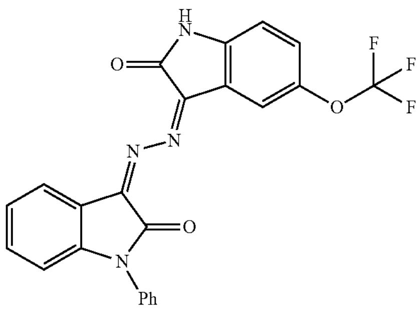 [SMILES: O=C1Nc2ccc(OC(F)(F)F)cc2/C1=N/N=C1\C(=O)N(c2ccccc2)c2ccccc21] | 7.67 ± 0.88 | 4.80 ± 0.12 | 1.60 |
| 18 | 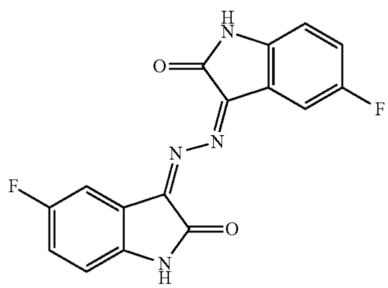 [SMILES: O=C1Nc2ccc(F)cc2/C1=N/N=C1\C(=O)Nc2ccc(F)cc21] | 20.42 ± 4.62 | 16.54 ± 6.28 | 1.23 |
| 19 | 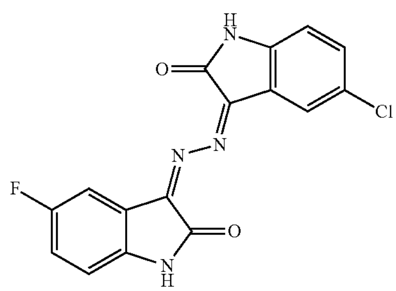 [SMILES: O=C1Nc2ccc(F)cc2/C1=N/N=C1\C(=O)Nc2ccc(Cl)cc21] | 17.40 ± 4.41 | 11.28 ± 3.26 | 1.54 |
| 20 | 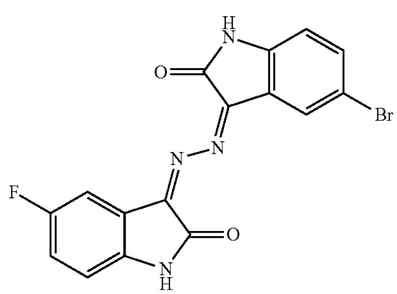 [SMILES: O=C1Nc2ccc(F)cc2/C1=N/N=C1\C(=O)Nc2ccc(Br)cc21] | 15.39 ± 3.97 | 18.64 ± 2.01 | 0.83 |
| 21 | 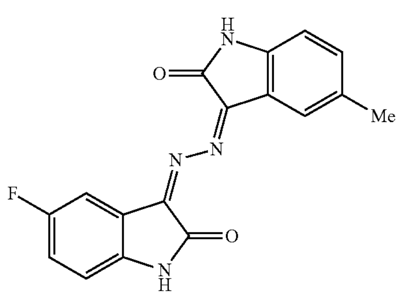 [SMILES: Cc1ccc2c(c1)/C(=N/N=C1\C(=O)Nc3ccc(F)cc31)C(=O)N2] | 18.92 ± 0.46 | 17.85 ± 0.82 | 1.06 |

TABLE 2-continued

Structure of compounds considered in this study, along with $IC_{50}$ values determined against the parental KB-3-1 cell line, and the P-glycoprotein-expressing cell line KB-V1[a]

| Compound | Structure | $IC_{50}$ KB3-1 (mM) | $IC_{50}$ KBV1 (mM) | RR |
|---|---|---|---|---|
| 22 | 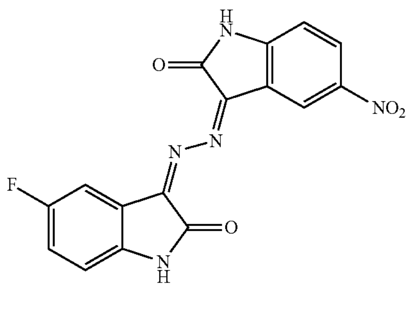 [SMILES: O=C1Nc2ccc(F)cc2/C1=N/N=C1\C(=O)Nc2ccc([N+](=O)[O-])cc21] | 56.00 ± 1.50 | 38.63 ± 13.54 | 1.45 |
| 23 | 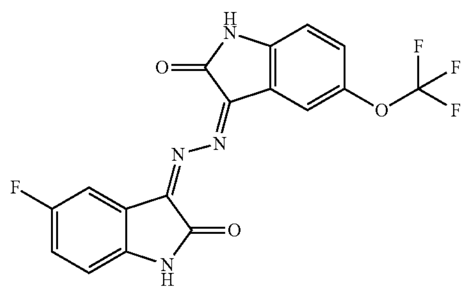 [SMILES: O=C1Nc2ccc(F)cc2/C1=N/N=C1\C(=O)Nc2ccc(OC(F)(F)F)cc21] | 15.23 ± 1.34 | 11.63 ± 2.55 | 1.31 |

[a] The MDR1 selectivity (RR) is calculated as the ratio of a compound's $IC_{50}$ against KB-3-1 cells divided by its $IC_{50}$ against KB-V1 cells. A value of >1 indicates that the compound kills P-gp-expressing cells more effectively than parental cells, so-called MDR1-selective activity. A value of <1 indicates that the P-gp-expressing cells are resistant to the compound, relative to parental cells, as is normally observed for P-gp substrates.
"N/A" denotes not tested for selectivity.

REFERENCES

J. Ahmedin, R. Siegel, E. Ward, Y. Hao, J. Xu, T. Murray, M. J. Thun, C A Cancer J Clin, 58, 71 (2008).
R. Sinha, K. El-Bayoumy, Current Cancer Drug Targets, 4, 13 (2004).
P. Cozzi, N. Mongelli, A. Suarato, Curr. Med. Chem.-Anti-Cancer Agents, 4, 93 (2004).
W. A. Milaat, Knowledge of secondary-school female students on breast cancer and breast selfexamination in Jeddah, Saudi Arabia. East. Mediterr. Health J., 6, 338-343 (2000).
A. A. Ezzat, E. M. Ibrahim, M. A. Raja, S. Al-Sobhi, A. Rostom, R. K. Stuart. Locally advanced breast cancer in Saudi Arabia: high frequency of stage III in a young population. Med. Oncol., 16, 95-103 (1999).
J. H. Talal. Adolescents and cancer: a survey of knowledge and attitudes a boutcancer in eastern provinceof saudi arabia. Saudi Soc. Family & Community Med., 7, 3 (2000).
http://www.who.int/ncd surveillance/infobase/web/InfoBasePolicyMaker/reports/ReporterFullVi ew.
http://www.gulfoncology.org/blog/2007/06/cancer-incidence-on-rise-in-saudi.html
M. Barinaga. From bench top to bedside. Science, 278, 1036-39 (1997)
J. M. Nabholtz, D. Slamon. Newadjuvant strategies for breast cancer: meeting the challenge of integrating chemotherapy and trastuzumab (Herceptin). Semin. Oncol. 28 (Suppl 3),1-12 (2001)
I. Pastan, R. J. Kreitman. Immunotoxins for targeted cancer therapy. Adv. Drug Deliv. Rev., 31, 53-88 (1998).
Druker B J, Sawyers C L, Kantarjian H, et al. Activity of a specific inhibitor of the BCR-ABL tyrosine kinase in the blast crisis of chronic myeloid leukemia and acute lymphoblastic leukemia with the Philadelphia chromosome. N. Engl. J. Med. 344, 1038-42 (2001).
I. Akan, S. Akan, H. Akca, B. Savas, T. Ozben, Nacetylcysteine enhances multidrug resistance-associated protein mediated doxorubicin resistance. Eur. J. Clin. Invest. 34, 683-689((2004).
I. Akan, S. Akan, H. Akca, B. Savas, T. Ozben, Multidrug resistance-associated protein 1 (MRP1) mediated vincristine resistance: effects of N-acetylcysteine and Buthionine sulfoximine. Cancer Cell Int. 5, 22 (2005).
M. Liscovitch, Y. Lavie, Cancer multidrug resistance: a review of recent drug discovery research. IDrugs. 5, 349-355 (2002).
H. Thomas, H. M. Coley, Overcoming multidrug resistance in cancer: an update on the clinical strategy of inhibiting p-glycoprotein. Cancer Control 10, 159-165 (2003).
C. H. Choi, ABC transporters as multidrug resistance mechanisms and the development of chemosensitizers for their reversal. Cancer Cell Int. 5, 30 (2005).
S. V. Ambudkar, S. Dey, C. A. Hrycyna, M. Ramachandra, I. Pastan, M. M. Gottesman, Biochemical, cellular, and pharmacological aspects of the multidrug transporter. Annu Rev. Pharmacol. Toxicol. 39, 361-398 (1999).
R. Krishna, L. D. Mayer, Multidrug resistance (MDR) in cancer. Mechanisms, reversal using modulators of MDR and the role of MDR modulators in influencing the pharmacokinetics of anticancer drugs. Eur. J. Pharm. Sci. 11, 265-283 (2000).
A. A. Stavrovskaya, Cellular mechanisms of multidrug resistance of tumor cells. Biochemistry (Mosc). 65, 95-106 (2000).

S. Grimaudo, M. Tolomeo, A. Chimirri, M. Zappala, R. A. Gancitano, N. D'Alessandro, European Journal of Cancer, 34, 1756 (1998).

Z. H. Zhu, In Dan Xi Xin Fa; Y. Wang, J. P. Zhu, L. Z. Jiang, Eds.; People's medical publishing, 2005, ISBN 7-1,7-06711-X/R__6712.

W. Tang, G. Eisenbrand, Chinese drugs of plant origin: Chemistry, Pharmacology, and Use in Traditional and Modern Medicine; Springer: Berlin, Heidelberg, New York, 1990.

H. A. Abdel-Aziz, A. Bari, T. Aboul-Fadl and S. Weng Ng. Acta Crystallographica Section E (2010).

J. A. Ludwig, G. Szakacs, S. E. Martin, B. F. Chu, C. Cardarelli, Z. E. Sauna, N. J. Caplen, H. M. Fales, S. V. Ambudkar, J. N. Weinstein, J. N.; Gottesman. Cancer Res., 66, 4808 (2006).

The invention claimed is:

1. A compound of Formula (I)

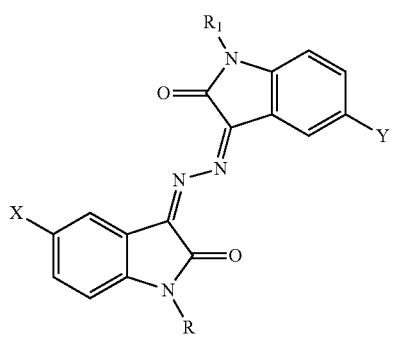

wherein
R is selected from the group consisting of hydrogen atom and unsubstituted or substituted phenyl group;
$R_1$ is selected from the group consisting of hydrogen atom and unsubstituted or substituted phenyl group;
X is selected from the group consisting of hydrogen atom or halogen atom; and
Y is selected from the group consisting of hydrogen atom, halogen atom, $C_1$-$C_4$ alkyl group, nitro group, and —$OCF_3$ group,
wherein the compounds in which R, $R_1$, X and Y are hydrogen atoms and in which R and $R_1$ are hydrogen atoms and X and Y are bromine atoms are excluded.

2. The compound according to claim 1, wherein R is selected from the group consisting of hydrogen atom and unsubstituted phenyl group.

3. The compound according to claim 1, wherein $R_1$ is selected from the group consisting of hydrogen atom and unsubstituted phenyl group.

4. The compound according to claim 1, wherein X is selected from the group consisting of hydrogen atom and fluorine atom.

5. The compound according to claim 1, wherein Y is selected from the group consisting of hydrogen atom, fluorine atom, chlorine atom, bromine atom, methyl group, nitro group and —$OCF_3$ group.

6. A pharmaceutical composition comprising the compound of Formula (I)

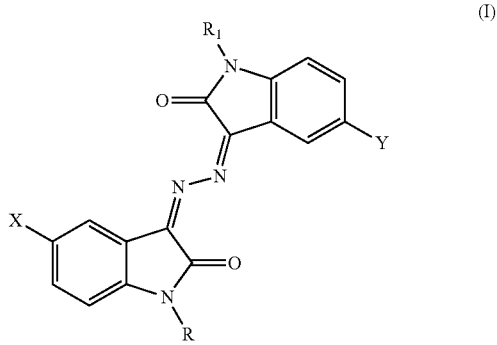

and at least one pharmaceutically acceptable excipient, wherein
R is selected from the group consisting of hydrogen atom and unsubstituted or substituted phenyl group;
$R_1$ is selected from the group consisting of hydrogen atom and unsubstituted or substituted phenyl group;
X is selected from the group consisting of hydrogen atom or halogen atom; and Y is selected from the group consisting of hydrogen atom, halogen atom, $C_1$-$C_4$ alkyl group, nitro group, and —$OCF_3$ group wherein the compounds in which R, $R_1$, X, and Y are hydrogen atoms and in which R and $R_1$ are hydrogen atoms and X and Y are bromine atoms are excluded.

7. A method of making a pharmaceutical composition comprising:
combining a compound of Formula (I)

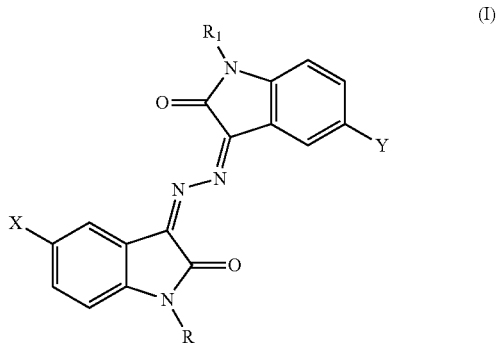

wherein
R is selected from the group consisting of hydrogen atom and unsubstituted or substituted phenyl group;
$R_1$ is selected from the group consisting of hydrogen atom and unsubstituted or substituted phenyl group;
X is selected from the group consisting of hydrogen atom or halogen atom; and
Y is selected from the group consisting of hydrogen atom, halogen atom, $C_1$-$C_4$ alkyl group, nitro group, and —$OCF_3$ group; and
a pharmaceutically acceptable excipient wherein the compounds in which R, $R_1$, X, and Y are hydrogen atoms and in which R and $R_1$ are hydrogen atoms and X and Y are bromine atoms are excluded.

8. A method of therapeutic treatment of cancer comprising administering to a patient in need thereof an effective amount of the compound of Formula (I)

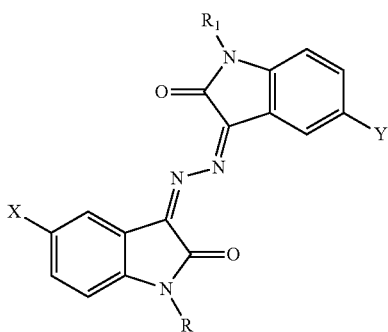

wherein
R is selected from the group consisting of hydrogen atom and unsubstituted or substituted phenyl group;
$R_1$ is selected from the group consisting of hydrogen atom and unsubstituted or substituted phenyl group;
X is selected from the group consisting of hydrogen atom or halogen atom; and
Y is selected from the group consisting of hydrogen atom, halogen atom, $C_1$-$C_4$ alkyl group, nitro group, and —$OCF_3$ group.

9. The method of claim 8 wherein the therapeutic treatment treats multidrug resistant cancer.

10. The method of claim 8, wherein the compounds in which R, $R_1$, X and Y are hydrogen atoms and in which R and $R_1$ are hydrogen atoms and X and Y are bromine atoms are excluded.

11. The method of claim 10 wherein the therapeutic treatment treats multidrug resistant cancer.

* * * * *